US011442128B2

(12) United States Patent
Bigot et al.

(10) Patent No.: US 11,442,128 B2
(45) Date of Patent: Sep. 13, 2022

(54) METHOD FOR FILTERING ERRONEOUS PIXELS IN A THERMAL THERAPY CONTROL SYSTEM

(71) Applicant: Profound Medical Inc., Mississauga (CA)

(72) Inventors: Alexandre Bigot, Toronto (CA); Benjamin Yat-Chung Leung, Toronto (CA)

(73) Assignee: Profound Medical Inc., Mississauga (CA)

( * ) Notice: Subject to any disclaimer, the term of this patent is extended or adjusted under 35 U.S.C. 154(b) by 349 days.

(21) Appl. No.: 16/589,784

(22) Filed: Oct. 1, 2019

(65) Prior Publication Data

US 2021/0093896 A1   Apr. 1, 2021

(51) Int. Cl.
*G01R 33/56* (2006.01)
*A61N 7/02* (2006.01)
*G01R 33/44* (2006.01)
*A61B 5/00* (2006.01)
*A61B 5/01* (2006.01)
(Continued)

(52) U.S. Cl.
CPC .......... *G01R 33/5608* (2013.01); *A61B 5/055* (2013.01); *A61N 7/02* (2013.01); *G01R 33/443* (2013.01); *G01R 33/4804* (2013.01); *G16H 20/30* (2018.01); *G16H 30/40* (2018.01); *A61B 5/015* (2013.01); *A61B 5/4836* (2013.01); *A61B 34/10* (2016.02); *A61B 2018/00547* (2013.01); *A61B 2034/107* (2016.02);
(Continued)

(58) Field of Classification Search
CPC ........ A61N 7/02; G16H 20/30; A61B 5/4836; A61B 5/015; A61B 5/055; A61B 2576/00–026; G01R 33/5608
See application file for complete search history.

(56) References Cited

U.S. PATENT DOCUMENTS 6,589,174 B1   7/2003   Chopra et al.
7,771,418 B2   8/2010   Chopra et al.
(Continued)

FOREIGN PATENT DOCUMENTS

WO   2015015307 A2   2/2015
WO   2019077385 A1   4/2019
WO   2019086921 A1   5/2019

OTHER PUBLICATIONS

ISA, "International Search Report", PCT/CA20/51300, dated Jan. 5, 2021.

*Primary Examiner* — Catherine B Kuhlman
*Assistant Examiner* — Andrew W Begeman
(74) *Attorney, Agent, or Firm* — Intrinsic Law Corp.

(57) ABSTRACT

During the delivery of thermal therapy, the measured temperature at each pixel in a cross-sectional temperature slice of a multi-pixel thermal image is compared to a maximum temperature limit. When the measured temperature of a pixel is higher than the maximum temperature limit for a predetermined number of consecutive cross-sectional temperature slices, the pixel is masked if the absolute value of the average difference between the measured temperature at the pixel and the measured temperatures at the pixel's neighbors is greater than a maximum temperature variation. The measured temperature of the masked pixel is ignored in subsequent cross-sectional temperature slices until the delivery of thermal therapy is complete.

18 Claims, 14 Drawing Sheets

(51) Int. Cl.
  *G16H 20/30* (2018.01)
  *G16H 30/40* (2018.01)
  *A61B 5/055* (2006.01)
  *G01R 33/48* (2006.01)
  *A61B 18/00* (2006.01)
  *A61B 34/10* (2016.01)
  *A61B 90/00* (2016.01)

(52) U.S. Cl.
  CPC ..... *A61B 2090/374* (2016.02); *A61B 2576/02* (2013.01); *A61N 7/022* (2013.01)

(56) References Cited

U.S. PATENT DOCUMENTS

| | | |
|---|---|---|
| 8,998,889 B2 | 4/2015 | Mahon et al. |
| 9,566,455 B2 | 2/2017 | Mahon et al. |
| 9,707,413 B2 | 7/2017 | Chopra et al. |
| 9,931,523 B2 | 4/2018 | Mahon et al. |
| 2007/0239062 A1 | 10/2007 | Chopra et al. |
| 2011/0034833 A1 | 2/2011 | Chopra et al. |
| 2011/0237930 A1 | 9/2011 | Donaldson et al. |
| 2011/0270366 A1 | 11/2011 | Mahon et al. |
| 2014/0267769 A1* | 9/2014 | Pillans .................. G06T 5/002 348/166 |
| 2019/0117108 A1 | 4/2019 | Bigot et al. |
| 2019/0125253 A1 | 5/2019 | Bigot et al. |

\* cited by examiner

1300

|   | A | B | C | D |
|---|---|---|---|---|
| 1 |   |   |   |   |
| 2 |   | 66°C | 68°C | 69°C |
| 3 |   | 64°C | 88°C | 67°C |
| 4 |   | 72°C | 90°C | 70°C |
| 5 |   |   |   |   |

FIG. 13

METHOD FOR FILTERING ERRONEOUS PIXELS IN A THERMAL THERAPY CONTROL SYSTEM

TECHNICAL FIELD

This invention relates to process controls and controllers for thermal therapy delivered by a treatment apparatus to target tissue based on temperature feedback data.

BACKGROUND

Magnetic resonance imaging (MRI) is used to obtain temperature related data during a thermal therapy procedure. Temperature measurements derived from MRI methods are subject to errors or potential errors from a variety of sources. These errors or potential errors can create temperature measurement uncertainty and/or significantly reduce the accuracy of measuring temperature changes.

When temperature measurements are used as part of a feedback system for thermal energy delivery, reduced accuracy in the temperature measurements can make it more difficult to determine whether there has been a lack of heating in a target region, an overheating of the target region, and/or an unintended heating of any other regions. Lack of heating in a target region can result in an incomplete thermal therapy session. Overheating in the target region can result in boiling which can reduce the transfer of thermal energy and lengthen the thermal therapy session. Unintended heating of other regions may cause damage to tissue and organs that are located near the target region. Mitigating both overheating and unintended heating require that thermal therapy be halted, at least temporarily, in order to allow such regions to cool. This can result in a less than optimal thermal therapy session from a patient comfort perspective, as well as less economical use of the MRI-thermal therapy facility, personnel and equipment, or even damage to healthy tissue near the target region.

It would be desirable to improve the accuracy of the temperature measurements and/or the process controls that rely on temperature measurements.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

One or more embodiments are directed to a method for controlling thermal therapy, comprising using a thermal therapy applicator, delivering a thermal therapy dose to a target volume within a patient's body; and in a computer receiving, at a first point in time, a first cross-sectional slice of temperature data for pixels corresponding to respective spatial locations in the target volume; for each pixel in the first cross-sectional slice, determining whether a measured temperature is higher than a maximum temperature limit; when the measured temperature at a first pixel in the first cross-sectional slice is greater than the maximum temperature limit, increasing a first pixel counter; when the first pixel counter is higher than a persistent threshold count, calculating an average temperature difference between the measured temperature at the first pixel in the first cross-sectional slice and the measured temperatures at neighboring pixels in the first cross-sectional slice; applying a mask to the first pixel when an absolute value of the average temperature difference is greater than a maximum temperature difference; and ignoring the measured temperatures at the masked first pixel in subsequent cross-sectional slices received at subsequent points in time, the subsequent points in time occurring after the first point in time.

Yet other embodiments are directed to a system for controlling a thermal therapy, comprising a computer having at least a processor, a data store and a data communication interface; the computer configured and arranged to execute in said processor, machine-readable instructions, and to operate on data obtained over said data communication interface and stored in said data store; the computer further configured and arranged as above to receive, at a first point in time, a first cross-sectional slice of temperature data for pixels corresponding to respective spatial locations in the target volume; for each pixel in the first cross-sectional slice, determining whether a measured temperature is higher than a maximum temperature limit; when the measured temperature at a first pixel in the first cross-sectional slice is greater than the maximum temperature limit, increasing a first pixel counter; when the first pixel counter is higher than a persistent threshold count, calculating an average temperature difference between the measured temperature at the first pixel in the first cross-sectional slice and the measured temperatures at neighboring pixels in the first cross-sectional slice; applying a mask to the first pixel when an absolute value of the average temperature difference is greater than a maximum temperature variation; and ignoring the measured temperatures at the masked first pixel in subsequent cross-sectional slices received at subsequent points in time, the subsequent points in time occurring after the first point in time.

BRIEF DESCRIPTION OF THE DRAWINGS

For a fuller understanding of the nature and advantages of the present invention, reference is made to the following detailed description of preferred embodiments and in connection with the accompanying drawings, in which:

FIG. 13 is an example thermometry slice in a dynamic according to one or more embodiments.

DETAILED DESCRIPTION

While delivering thermal therapy to a target volume within a patient's body, the temperature of the target volume is analyzed as a feedback control. The analysis includes determining if the measured temperature, at a pixel in a cross-sectional temperature slice of a multi-pixel thermal image, is higher than a maximum temperature limit for a predetermined number of consecutive cross-sectional temperature slices. When the measured temperature at the pixel is higher than the maximum temperature limit for a predetermined number of consecutive cross-sectional temperature slices, the pixel's measured temperature is compared to the neighboring pixels' measured temperatures. If there is a significant difference between the pixel's measured temperature and the neighboring pixels' measured temperatures, the pixel is masked and ignored until the thermal therapy delivery is complete. A persistently hot pixel, combined with a significant difference between the pixel's measured temperature and the neighboring pixels' measured temperatures, indicates that the pixel's measured temperature is noisy or inaccurate and potentially unreliable for purposes of process control. Some causes of inaccurate pixel readings can include calcifications, tissue motion and other causes. Ignoring such a noisy and unreliable pixel can reduce the need to pause thermal therapy delivery due to inaccurate temperature measurements. Thermal therapy delivery can be paused when the measured temperature at a pixel is higher than a maximum temperature limit to avoid heating the tissue and/or fluid in the target volume to its/their boiling point (e.g., which occurs at approximately 100° C.). An inaccurate temperature measurement can cause the thermal therapy delivery to be paused unnecessarily, which can lengthen the time needed to deliver a therapeutic dose of thermal therapy and increase the associated costs.

In one example, the average difference between the pixel's measured temperature and each neighboring pixel's measured temperature is determined. When the absolute value of the average difference between the pixel's measured temperature and each neighboring pixel's measured temperature is greater than a maximum temperature variation (e.g., from about 10° C. to about 16° C.), the pixel is masked.

Figure 1:
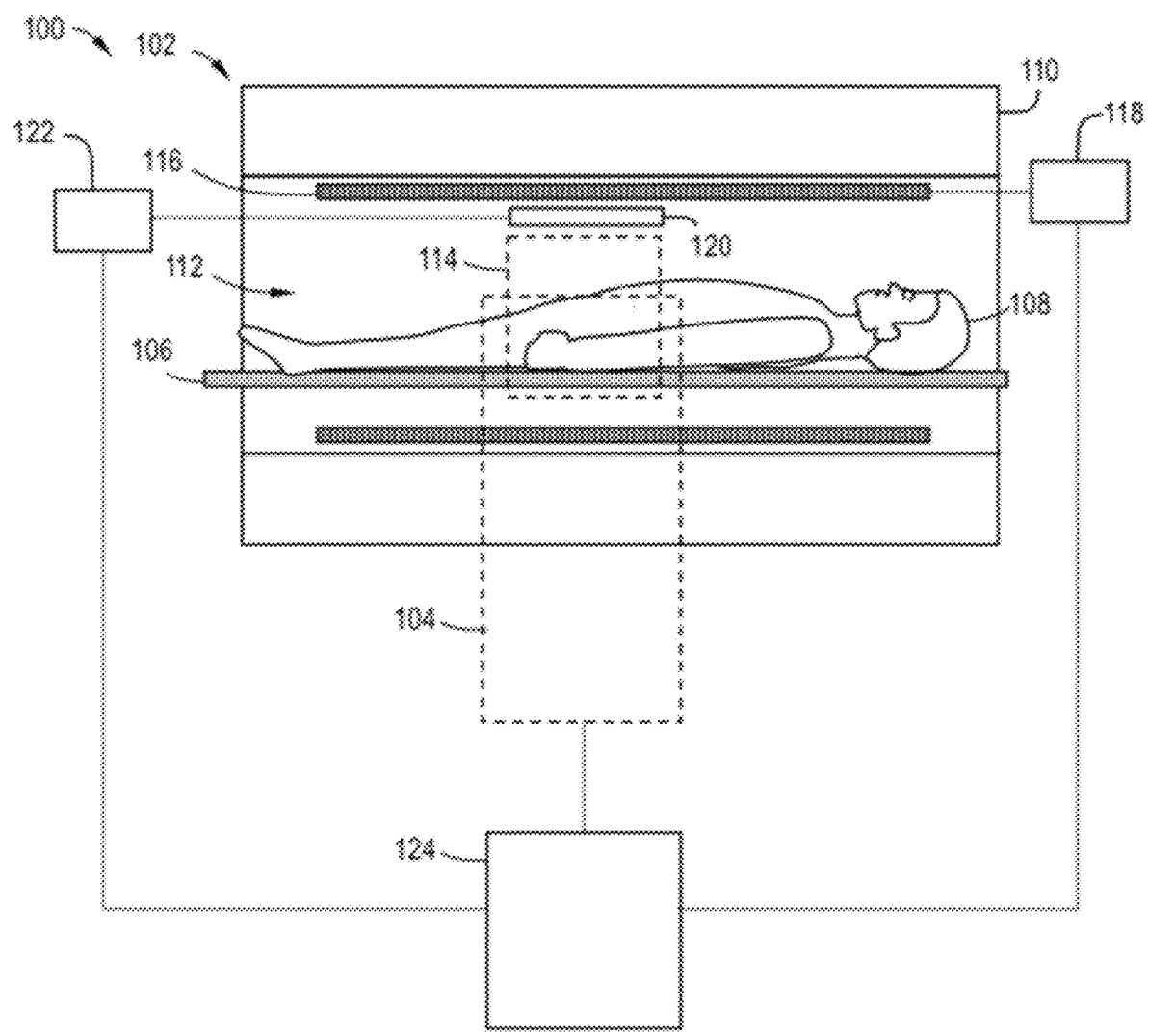
FIG. 1 illustrates an example of a medical system in which at least some embodiments disclosed herein are employed.

FIG. 1 illustrates an example of a medical system 100 in which at least some embodiments disclosed herein are employed. The medical system 100 includes a patient support 106, on which a patient 108 can be disposed, a magnetic resonance imaging (MRI) system 102, and an image-guided thermal therapy system 104.

The MRI system 102 includes a magnet 110 disposed about an opening 112, an imaging zone 114 in which the magnetic field is strong and uniform enough to perform magnetic resonance imaging, a set of magnetic field gradient coils 116 to acquire magnetic resonance data 114, a magnetic field gradient coil power supply 118 that supplies current to the magnetic field gradient coils 116 and is controlled as a function of time, a radio-frequency coil 120 to manipulate the orientations of magnetic spins within the imaging zone 114, a radio frequency transceiver 122 connected to the radio frequency coil 120, and a computer 124, which performs tasks (by executing instructions and/or otherwise) to facilitate operation of the MRI system 102 and is coupled to the radio frequency transceiver 122, the magnetic field gradient coil power supply 118, and the image-guided thermal therapy treatment system 104.

The image-guided thermal therapy system 104 can perform image-guided thermal therapy and can implement one or more aspects and/or embodiments disclosed herein (or portion(s) thereof) to reduce the effects of errors and/or potential errors in temperature measurements (e.g., based on magnetic resonance (MR) thermometry) in the target region or volume. The image-guided thermal therapy system 104 can have various operating modes.

In at least some embodiments, the computer 124 of the MRI system 102 and/or one or more other computing devices (not shown) in and/or coupled to the system 100 may also perform one or more tasks (by executing instructions and/or otherwise) to implement one or more aspects and/or embodiments disclosed herein (or portion(s)) thereof to reduce the effects of errors and/or potential errors in temperature measurement (e.g., based on MR thermometry) in the target region or volume.

Figure 2:
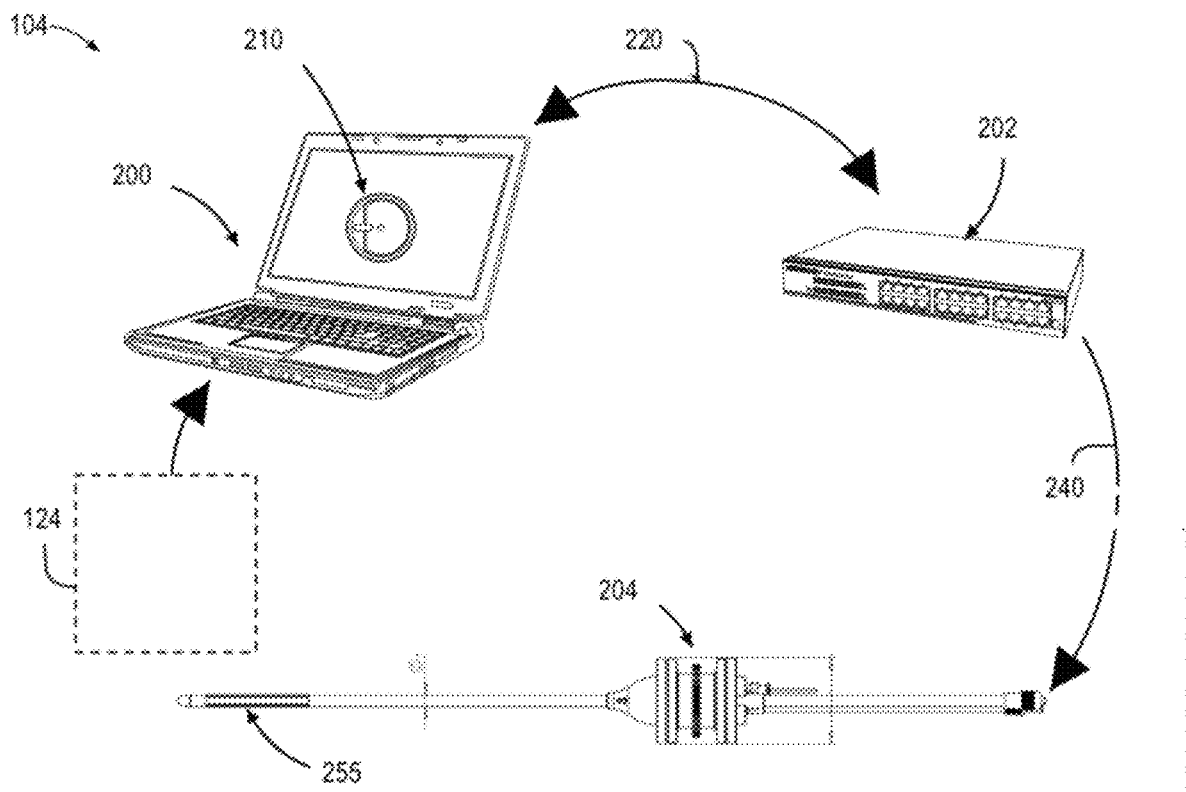
FIG. 2 is a stylized diagram of an implementation of the image-guided thermal therapy system illustrated in FIG. 1, in accordance with at least some embodiments.

FIG. 2 is a stylized diagram of an implementation of the image-guided thermal therapy system 104, in accordance with at least some embodiments. The image guided thermal therapy system 104 includes a system controller 200, a therapy apparatus controller 202, and a therapy apparatus 204. The system controller 200 (which may comprise a portable PC, workstation, or any other type of processing device) can perform tasks (e.g., by executing instructions and/or otherwise) to facilitate operation of the image-guided thermal therapy system 104 and to implement one or more aspects and/or embodiments disclosed herein (or portion(s) thereof) to reduce the effects of errors and/or potential errors in temperature measurement (e.g., based on MR thermometry) in the target region or volume. The system controller 200 can include a display and/or user interface 210 to facilitate user control of and/or observation of the thermal therapy treatment process, and it can be coupled to and supply signals to the therapy apparatus controller 202 via communication link 220. The therapy apparatus controller 202 (which may be part of the system controller 200) can comprise analog and/or digital circuitry to determine and/or provide drive signals to be supplied to the therapy apparatus 204, and can be coupled to the therapy apparatus 204 via a power or other communication link 240.

The therapy apparatus 204 (which can be positioned and/or rotated by a motor assembly coupled thereto) can comprise an ultrasound or other treatment apparatus configured to deliver a suitable dose of ultrasound or other energy (e.g., infrared light energy, radiation energy, electromagnetic energy, etc.) to tissue in a diseased region of a patient's body. In the illustrated embodiment, the therapy apparatus 204 comprises an elongated transurethral prostate therapy applicator having a portion 255 to be inserted longitudinally into a patient's prostate to deliver ultrasound energy to a diseased region of the patient's prostate.

The computer 124 of the MR system 102 (FIG. 1) can provide real-time (or other) images of relevant parts of the patient to the system controller 200 and/or the display and/or graphical user interface 210. The images can include phase data that can be used to determine the temperature of the corresponding spatial location in the patient. The system controller 200 can use the images to monitor (in real time or otherwise) the progress or other status of the thermal therapy and may generate signals based at least in part thereon to control the therapy apparatus controller 202. Information indicative of the progress or other status may also be provided to a clinical or other operator, who may provide input (to the system controller 200 and/or the therapy apparatus controller 202) to adjust or otherwise control the thermal therapy.

Figure 3:
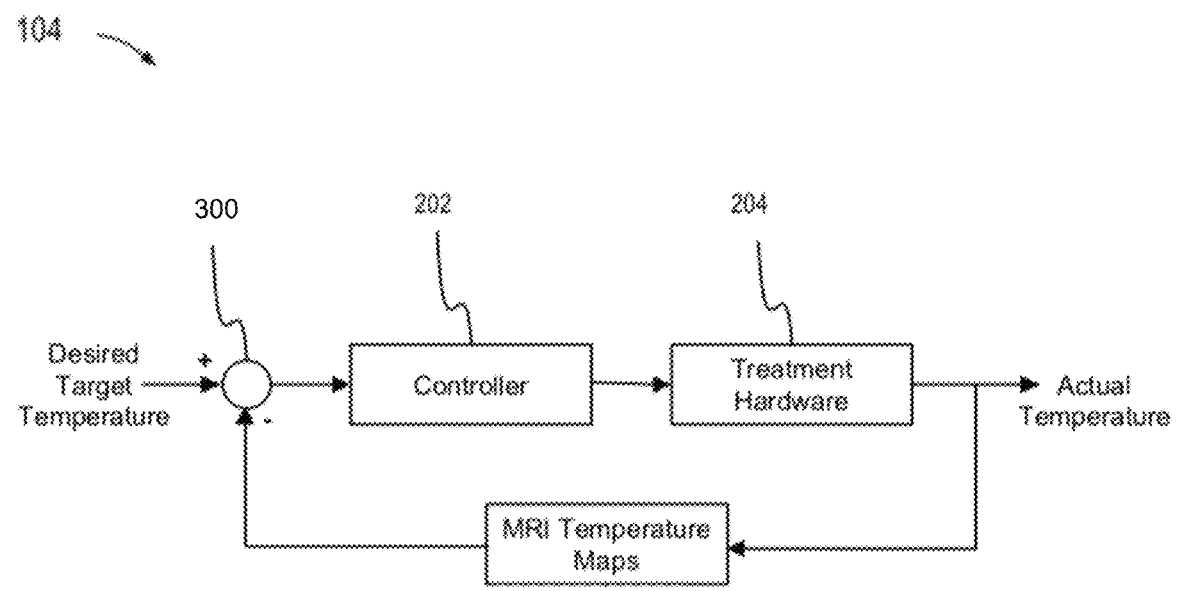
FIG. 3 is a schematic diagram of a portion of the image-guided thermal therapy system illustrated in FIGS. 1 and 2 in one operating mode in accordance with at least some embodiments.

FIG. 3 is a schematic diagram of a portion of the image-guided thermal therapy system 104 in one operating mode in accordance with at least some embodiments.

Referring to FIG. 3, the portion of the system 104 includes an error amplifier 300 (which can be located in the system controller 200 or in the therapy apparatus controller 202) that receives a signal indicative of a desired target temperature and further receives MRI temperature data (e.g., temperature maps or other temperature data generated based at least in part on MRI data such as MR thermometry data). An output from the error amplifier is supplied to the therapy apparatus controller 202, which generates drive signals that are based at least in part thereon and supplied to the therapy apparatus 204. The therapy apparatus 204 outputs ultrasonic energy (and/or other energy such as infrared light energy, radiation energy, and/or electromagnetic energy) based at least in part thereon to one or more target regions of a patient undergoing thermal treatment. The energy raises temperatures within the target region(s), which are imaged using MRI techniques. The MRI imaging is mapped to MRI temperature data, which is fed back to the error amplifier 300, which can adjust the output to the therapy apparatus controller 202 based at least in part thereon and/or as appropriate in subsequent steps of the treatment. This general method may be followed until the treatment goals are satisfied (e.g., a given temperature is reached in some or all of the target or treatment region(s)) or an alarm or other action interrupts the process.

Figure 4:
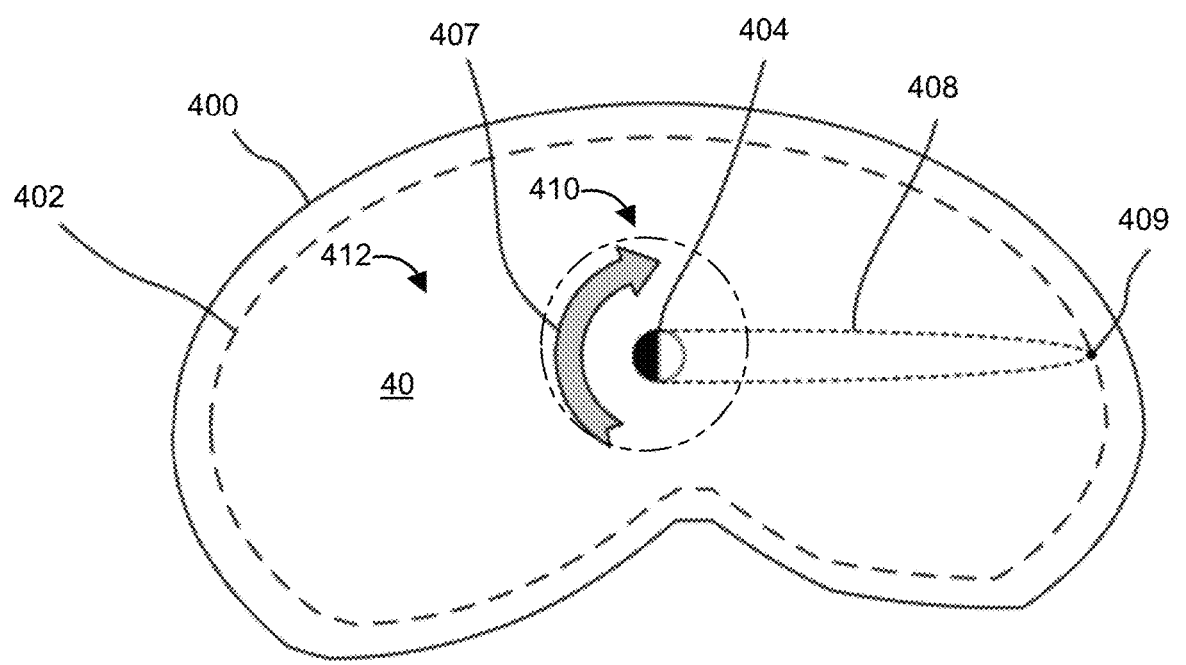
FIG. 4 illustrates a cross section of a prostate and an elongated transurethral prostate therapy applicator inserted longitudinally therein to allow performance of conformal thermal therapy to the prostate (or a portion thereof), shown at a time t0, in accordance with at least some embodiments.

FIG. 4 illustrates a cross section of a prostate 40 and an elongated transurethral prostate therapy applicator 404 inserted longitudinally therein to allow performance of conformal thermal therapy 408 to the prostate 40 (or a portion thereof), shown at a time t0, in accordance with at least some embodiments.

A treatment boundary 402, representing a desired treatment volume or a temperature control perimeter or surface, for example inside treatment organ boundary 400, may be defined in a treatment planning step prior to or during application of the thermal therapy treatment. In some aspects, the temperature control surface or perimeter represents an outline along which the system and method are used to control a temperature using the thermal therapy process. The treatment boundary 402 is defined a predetermined distance within the treatment organ boundary 400. For example, the treatment boundary 402 can be defined to be about 1 mm to about 4 mm, including about 2 mm and about 3 mm, inside the treatment organ boundary 400. As used herein, "about" means plus or minus 10% of the relevant value or number.

As represented in the figure, and according to certain designs of applicator 404, the thermal therapy 408 may be directionally emitted from an active face of applicator 404. In view at least thereof, the location/direction of the thermal therapy 408 at any given point in time, and the location of the control point 409 at any given point in time, may depend on the angular position of applicator 404. The thermal therapy 408 is represented in the figure by a flame-shaped profile or zone (sometimes referred to herein as a treatment zone lobe) extending from the applicator 404, however the thermal therapy 408 is not limited and may instead have any suitable configuration.

In at least some embodiments, the thermal therapy applicator 404 may be rotated about its axis using a computer-controlled motor so as to sweep through the treatment volume defined by the treatment boundary 402, for example as described in U.S. Pat. Nos. 6,589,174 and 7,771,418; U.S. Application Publication Nos. 2007/0239062 and 2011/0034833; and U.S. patent application Ser. Nos. 12/932,914, 12/932,923, 12/932,920, and 13/065,106, which are all hereby incorporated by reference.

The rotation 407 may be performed at any rate(s), which may be predetermined (e.g., planned) and/or determined dynamically during the therapy process. In at least some embodiments, the applicator 404 rotates in a clockwise direction 407 as shown, but it is not limited to such.

In at least some embodiments, the treatment boundary 402 is an intended boundary within which the energy of the thermal therapy process is substantially controlled to a set-point temperature (or thermal dose) ensuring rapid and sufficient cell death of diseased cells within the interior of the volume defined by the treatment boundary 402. Heat can be conducted outside the treatment boundary out to the boundary of an organ (e.g., the prostate), which can be measured and controlled to achieve appropriate thermal therapy while reasonably avoiding damage to non-diseased tissues and organs proximal to said diseased locations. Tissues and organs outside the treatment boundary 402, even if heated, should not exceed lethal thermal dose or temperature limits. The set-point temperature can be from about 50° C. to about 70° C. in some embodiments, including about 55° C., about 60° C., about 75° C., and any temperature or temperature range between any two of the foregoing temperatures.

In some embodiments, a central region 410 around the applicator 404 is excluded from temperature control of the thermal therapy process. In other words, the energy of the thermal therapy process can be substantially controlled to a set-point temperature (or thermal dose) ensuring rapid and sufficient cell death of diseased cells in a temperature control region 412 defined between the treatment boundary 402 and the central region 410. The central region 410 can be defined by a circle having a predetermined radius from the applicator 404. The predetermined radius can be about 4 mm to about 8 mm, including about 5 mm, about 6 mm, and about 7 mm.

Systems and methods for monitoring and/or controlling thermal therapy using ultrasound are described in, for example, U.S. patent application Ser. No. 15/797,075, titled "Thermal Therapy with Dynamic Anatomical Boundaries Using MRI-Based Temperature Uncertainty Maps," U.S. Patent Application Publication No. 2011/0270366, titled "RF Power Controller for Ultrasound Therapy System," and U.S. Pat. No. 8,998,889, titled "System and Method for Control and Monitoring of Conformal Thermal Therapy," which are hereby incorporated by reference.

Figure 5:
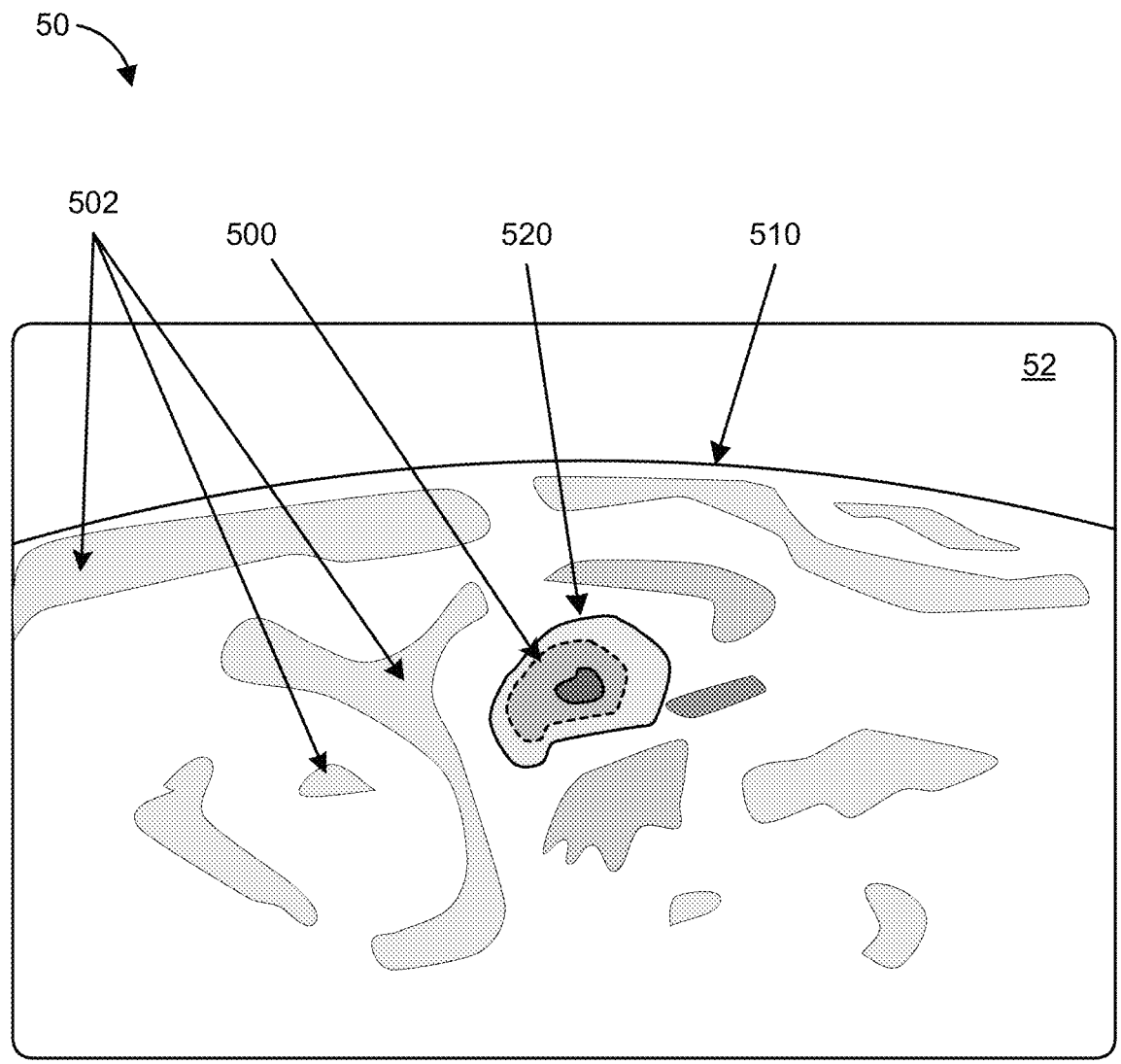
FIG. 5 illustrates an example of a temperature uncertainty map.

FIG. 5 illustrates a cross-sectional view, taken using an imaging modality such as an MRI system, of a portion of a patient's body in the vicinity of a treatment target volume. The scene shown includes for example a visual output device such as a computer monitor screen 50 or application window of a computer application program for displaying an image 52. The surface of the patient's body (e.g., the surface of his abdomen) is shown at 510 while various zones 502 in the patient's body are shown by a visual representation of their temperatures and/or temperature uncertainties within image 52. The temperatures can be determined by MR thermometry or other technique. The zones 502 can be displayed on the screen 50 as colored contours, contour plots, gray scale intensities or other visual representations of the temperature and/or temperature uncertainty.

The image 52 shows a boundary 520 of a target volume such as a male prostate or portion thereof. This is an outline on image 52, which can be computer-drawn or drawn with the assistance of an operator on the screen 50. A treatment target boundary 500 is further shown on the image 52, which can be a contour of another color, a dashed contour, or other representation. The target boundary 500 is the intended boundary within which the energy of the thermal treatment process is substantially controlled to a set-point temperature (or thermal dose) ensuring rapid and sufficient cell death of diseased cells within the interior of the volume defined by the target boundary 500. Heat can be conducted outside the target boundary 500 out to the boundary of the prostate 520, which can be measured and controlled to achieve appropriate thermal therapy while reasonably avoiding damage to non-diseased tissues and organs proximal to said diseased locations. Tissues and organs outside the target boundary, even if heated, will not exceed lethal thermal dose or temperature limits. In some embodiments, the target boundary 500 is the same as or different than the treatment boundary 402 (FIG. 4).

In all, FIG. 5 shows a temperature map and/or a temperature uncertainty map. Three-dimensional representations of the same can be constructed from additional layers, slices or cross-sectional views like that shown in FIG. 5. The methods described herein can therefore be generalized to three-dimensional space by stacking slices such as shown in FIG. 5 side by side to form a 3D volume without loss of generality. In some embodiments, each layer/slice can correspond to and/or can be associated with a corresponding ultrasound transducer element.

Figure 6:
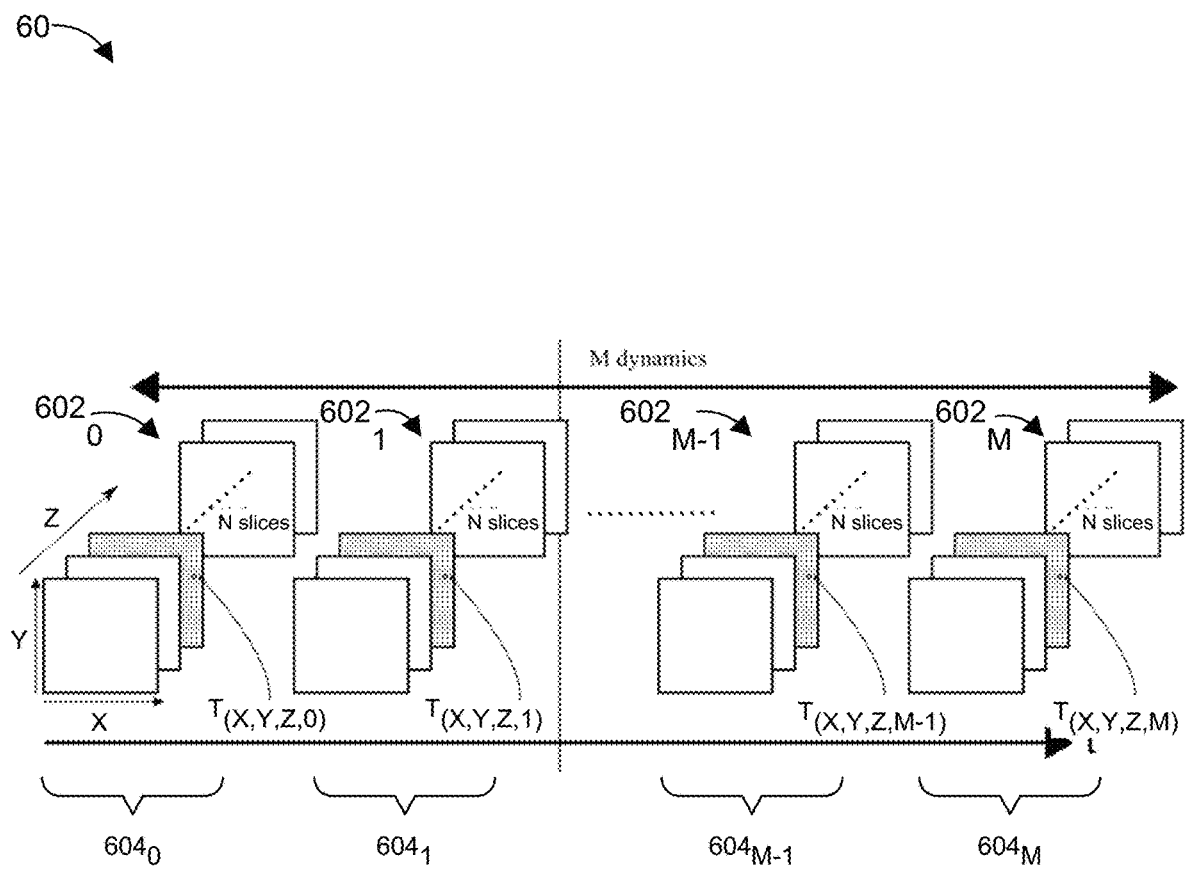
FIG. 6 is a representation of MRI image data that may be captured before, during and/or after thermal therapy, in accordance with at least some embodiments.

FIG. 6 is a representation 60 of MRI image data that may be captured before, during and/or after thermal therapy, in accordance with at least some embodiments.

The MRI image data includes sets of MRI image data $602_0$-$602_M$. Each set of MRI image data may include N images, e.g., cross sections (sometimes referred to as slices) of the target volume and surrounding areas and may be captured from an MRI device during a respective one of a plurality of collection periods, e.g., collection periods $604_0$-$604_M$. A collection period for a set of MRI image data is sometimes referred to herein as a "dynamic."

In at least some embodiments, each set of MRI image data may comprise 12 or any other specified number of slices. The amount of time, sometimes referred to herein as a "dynamic," needed to capture and/or receive the 12 or other specified number of slices in the set may average 4-6 seconds or other amount of time.

In at least some embodiments, one or more sets of MRI image data corresponding to one or more dynamics may be captured prior to the start of therapy (e.g., at collection period $604_0$) and used in determining a set of reference images. In at least some embodiments, the set of reference images will include one reference image for each slice in a set of MRI image data. In at least some embodiments, each reference image (phase or otherwise) may be generated by taking the mean of five or other number of images (phase or otherwise). Thus, in some embodiments, the set of reference images is based on the average temperature at each pixel in each slice across 5 (or other) reference dynamics. Those skilled in the art will understand that a different number of dynamics can be used here, which may depend on the computational efficiency of the system and other engineering or clinical requirements.

An "image" can be a representation (exact or otherwise (i.e., non-exact)) of one or more objects (e.g., a body (or portion(s) thereof) of a patient, data, or any other type of object(s)) and/or one or more characteristics thereof (e.g., temperature(s) and/or other physical characteristic(s)). An image may have any form(s). For example, some images may have the form of data that may be machine readable but need not be visible to a human eye.

An image may be received from any source(s). For example, an "MRI image" can be an image that is based at least in part on MRI data. A "phase image" can be an image that is based at least in part on phase data (e.g., from the MRI data). A "magnitude image" can an image based at least in part on magnitude data (e.g., from the MRI data). The terms "phase image" and "magnitude image" are not mutually exclusive. Thus, in at least some embodiments, an image may be both a "phase image" and a "magnitude image."

In at least some embodiments, after the start of therapy, an uncorrected temperature may be calculated or otherwise determined for each pixel (in any given measurement image) as a difference between a phase of the pixel in the measurement image and a phase of the same pixel in the corresponding reference image, multiplied by a constant. The phase differences that are determined for the plurality of pixels in any given measurement image are sometimes collectively referred to herein as a phase difference image (or a phase difference).

In at least some embodiments, phase images collected during a dynamic may be processed to form a temperature map. Each temperature map may be stored in a buffer that has a width of M temperature maps (corresponding to M dynamics) and may be used to hold a rolling window of M temperature maps that may be used to calculate a temperature uncertainty map and/or to perform process controls.

In at least some embodiments, the MR image data comprises measurements (of radio frequency signals emitted by atomic spins) recorded by the antenna of a magnetic resonance apparatus during a magnetic resonance imaging scan which contains information which may be used for MR thermometry. In at least some embodiments, MR thermometry functions by measuring changes in temperature sensitive parameters. Examples of such parameters are: the proton resonance frequency shift, the diffusion coefficient, or changes in the T1 and/or T2 relaxation time may be used to measure the temperature using magnetic resonance. One of the most useful of the above measures the proton resonance frequency (PRF) shift of water protons. The resonant frequency of the protons is temperature dependent. As temperature changes in a voxel (an element in an array of volume), the frequency shifts, which causes the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

At least some embodiments may rely on the proton resonant frequency shift which is known to vary with temperature according to the formula:

$$T = \frac{\Delta\emptyset}{\alpha \gamma B_0 TE} + BaseTemp$$

where T=temperature in degrees Celsius, $\Delta\emptyset$32 phase difference, $\alpha$=thermal shift coefficient (ppm/° C.), $\gamma$=gyromagnetic ratio for $H^+$ nuclei (MHz/Tesla), Bo=magnetic field strength (Tesla), TE=echo time (sec), and BaseTemp=base temperature in degrees Celsius.

Since the thermometry formula is based on the PRF-sensitivity of water content in tissues, in at least some embodiments, lipid and bone tissues produce unreliable temperature measurements which can be excluded from the thermometry region of interest when making temperature-based decisions.

Figure 7:
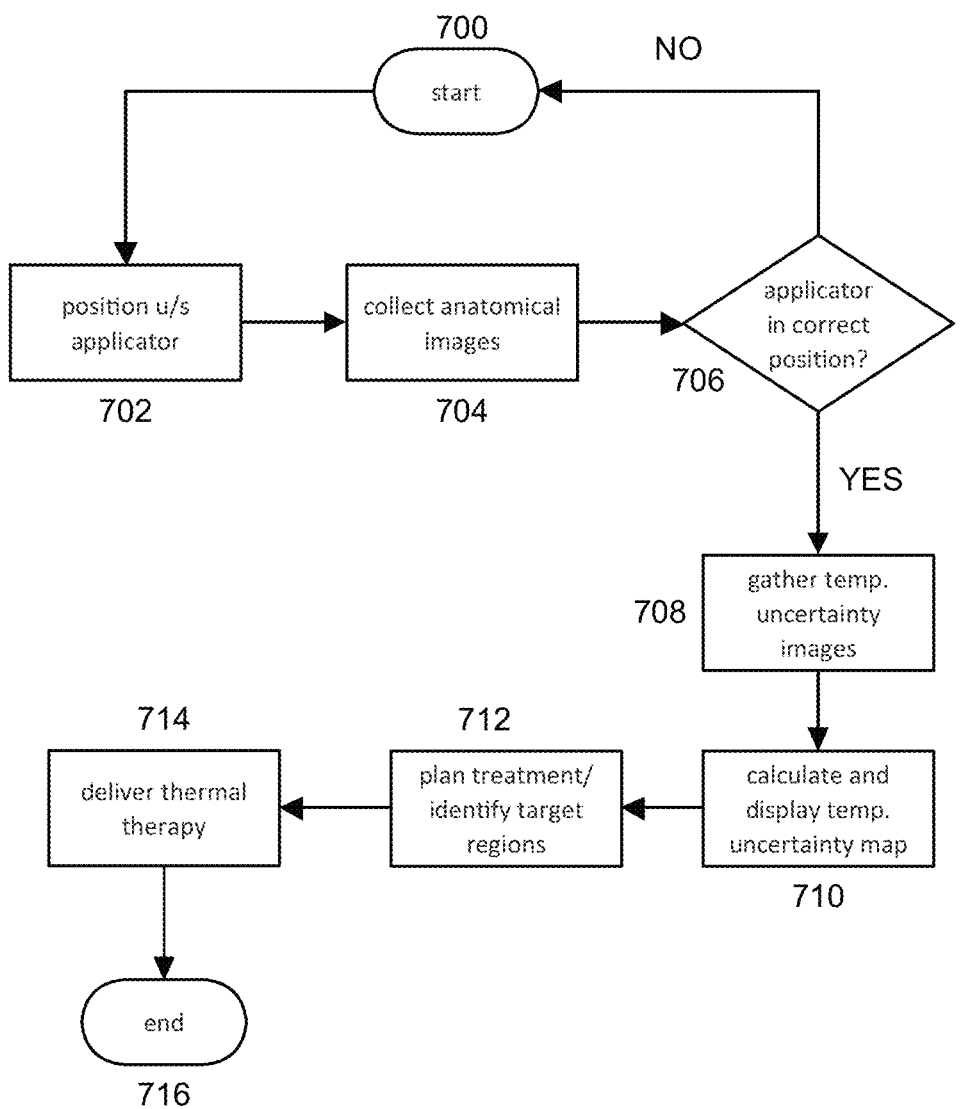
FIG. 7 illustrates an exemplary process for thermal treatment in an MRI-guided environment and accounting for temperature uncertainty in the MRI thermometry portion of the process.

FIG. 7 illustrates an exemplary process 70 for thermal treatment in an MRI-guided environment and accounting for temperature uncertainty in the MRI thermometry portion of the process. The process begins at step 700 and the thermal therapy device is positioned automatically or manually in or on the patient at step 702. In an example, an ultrasound thermal therapy applicator is inserted trans urethrally into a diseased male prostate organ and positioned so as to deliver thermal therapy to the diseased organ. In another aspect, the patient is placed in an MRI imaging volume or machine bore and temperature scans using MRI thermometry are obtained, slice by slice, through a target region to generate thermal imagery and/or temperature uncertainty maps of the target region.

Anatomical images of the patient or portion of the patient in the vicinity of the target region are obtained at step 704. The system can automatically or semi-automatically determine whether the thermal therapy applicator is in the correct position to deliver the desired thermal therapy to the target region at 706. If not, the process returns to position the thermal therapy applicator at 702.

Once the thermal therapy applicator device is in the correct position, temperature data is collected at 708. A memory or digital storage apparatus can be used to store the data for analysis or other purposes.

The system next calculates and displays the temperature uncertainty maps (e.g., as depicted in FIG. 5) at step 710. These are preferably output to a computer output or display device such as a computer workstation monitor connected to the imaging and therapy device in an overall thermal therapy control system.

Using the temperature data and temperature uncertainty maps, a thermal therapy treatment plan is determined and target points or target regions are identified at step 712.

The thermal therapy itself is delivered from a thermal therapy applicator, e.g., an ultrasound transducer array device in or proximal to the desired target region at step 714. During thermal therapy, additional temperature and temperature uncertainty images are gathered, displayed, and/or analyzed, as discussed below (e.g., as discussed with respect to FIGS. 9-11).

Once the thermal therapy procedure is complete, the system or operator terminates the process 70 at 716. The thermal therapy procedure can be complete when a predetermined thermal dose has been delivered to each location in the target region.

Figure 8:
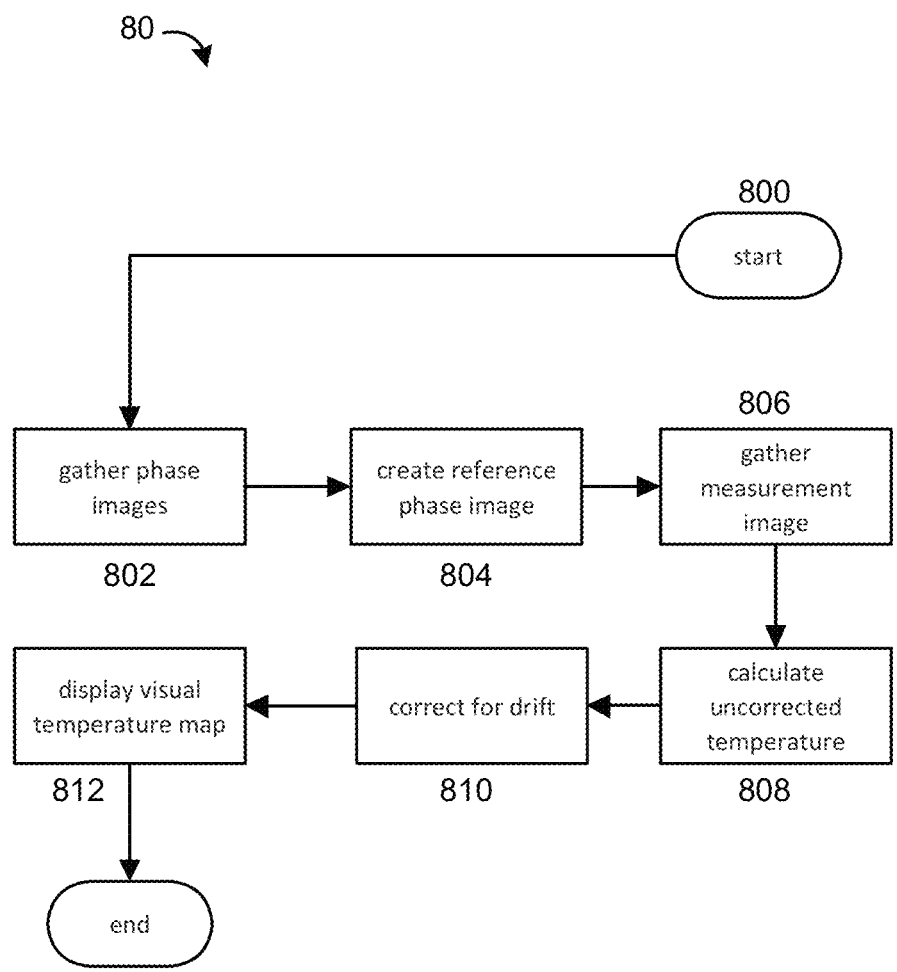
FIG. 8 illustrates another set of steps in an exemplary computer-implemented method for gathering images in the context of image-guided thermal therapy, making appropriate corrections and generating outputs for use in that context.

FIG. 8 illustrates another set of steps in an exemplary computer-implemented method 80 for gathering MR images in the context of image-guided thermal therapy, making appropriate corrections and generating outputs for use in that context.

The process starts at 800 and one or more phase images are gathered from an MRI device in which a patient is placed. In an embodiment, several (e.g., 3 to 10) phase images are gathered at step 802 and stored in a machine-readable storage device such as a computer memory device. The MRI device can be configured, arranged, programmed, and operated so as to run a sequence to output the magnitude and phase images in real time. The output images are output through a signal connection or network connection as desired, for example to another computer device, coupled to the MRI device, where subsequent computations and processing of the MRI data can be carried out.

In an example, an EPI sequence is used to gather the channel uncombined phase images. Other sequences can be used as would be understood by those skilled in the art, for example a GRE sequence.

In some thermal therapies using an ultrasound transducer system, multiple ultrasound transducer elements are deployed in an ultrasonic array placed within the diseased tissue volume. For multi-transducer ultrasound therapy systems, multiple image slices can be taken such that one image slice is taken per ultrasound transducer. In yet another aspect, a monitoring slice image can be taken at either end of the imaging slices for full monitoring. The sequence is set in an embodiment to automatically repeat so that stacks of phase images are generated continuously throughout the thermal therapy treatment.

A reference phase image is created at step 804 using data from the gathered phase images in the previous step. This reference phase image is the phase image prior to initiating heating from the thermal therapy procedure. To increase signal to noise, the reference phase image is calculated as the average phase over several (e.g., 5) reference images (e.g., taken over 5 dynamics) for each pixel in the image. Again, a different number of dynamics can be used in various embodiments as needed for engineering and/or clinical requirements.

A measurement image is collected at step 806 prior to and/or during the thermal therapy procedure. The system then calculates uncorrected temperatures at step 808. In an example, a weighted sum of the phase differences across all channels is calculated and scaled so as to determine temperatures. In an aspect, an MRI device can be programmed to output the combined phase for all coils. In this case the system only calculates the phase difference from the reference image to be scaled to output the temperature in a region of interest.

At step 810 the system corrects for magnetic field drift. Drift can be due to temporal changes or drift in the main B0 magnetic field of the MRI machine. The drift can result in erroneous (typically lower) temperature measurements if not corrected for. Drift effects can be corrected at one or more areas of the image. The temperature at these areas is assumed to be that of the patient's body's core temperature, which substantially does not change throughout a therapy treatment. In some embodiments, a linear or quadratic correction term may be calculated for each measurement slice image and added to the temperature at each pixel in the image to generate a drift-corrected temperature image.

In step 812, a visual temperature map is displayed on a display coupled to the computer. The data from a set of N drift-corrected temperature images for up to M dynamics can be stored in a buffer coupled to or in the computer.

Figure 9:
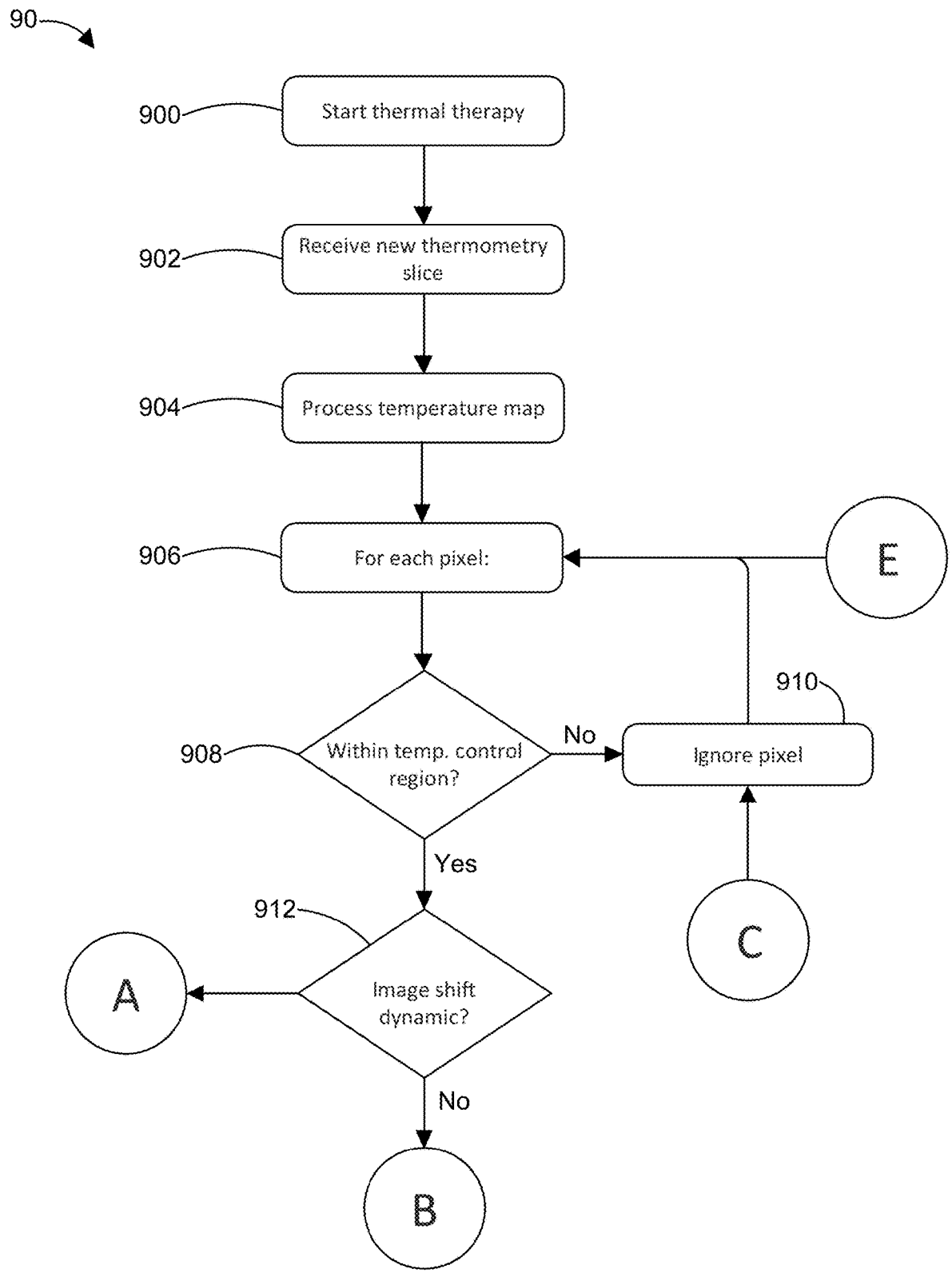
FIGS. 9, 10, and 11 are a flow chart for applying thermal therapy to a target volume with dynamic pixel masking.
Figure 10:
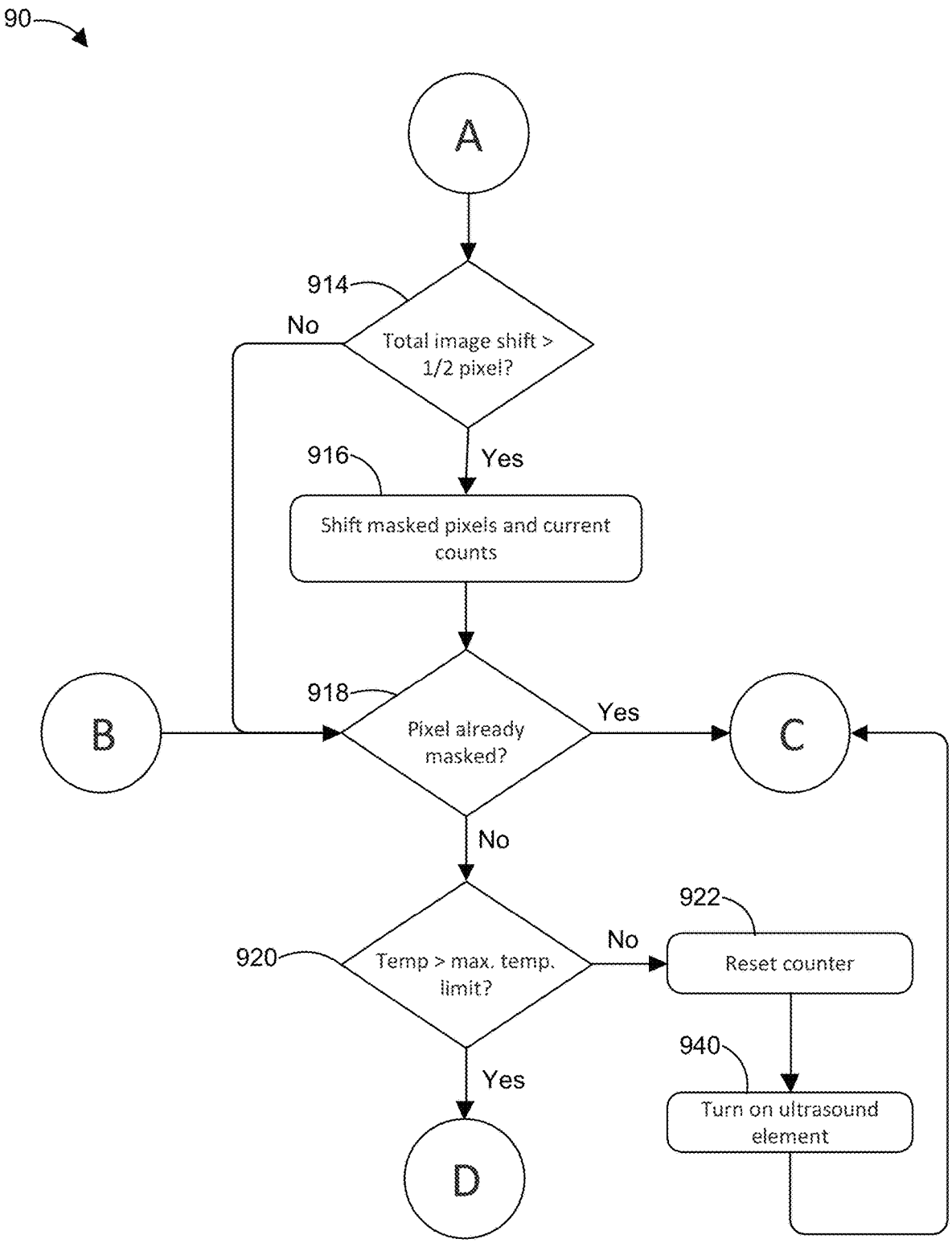
Figure 11:
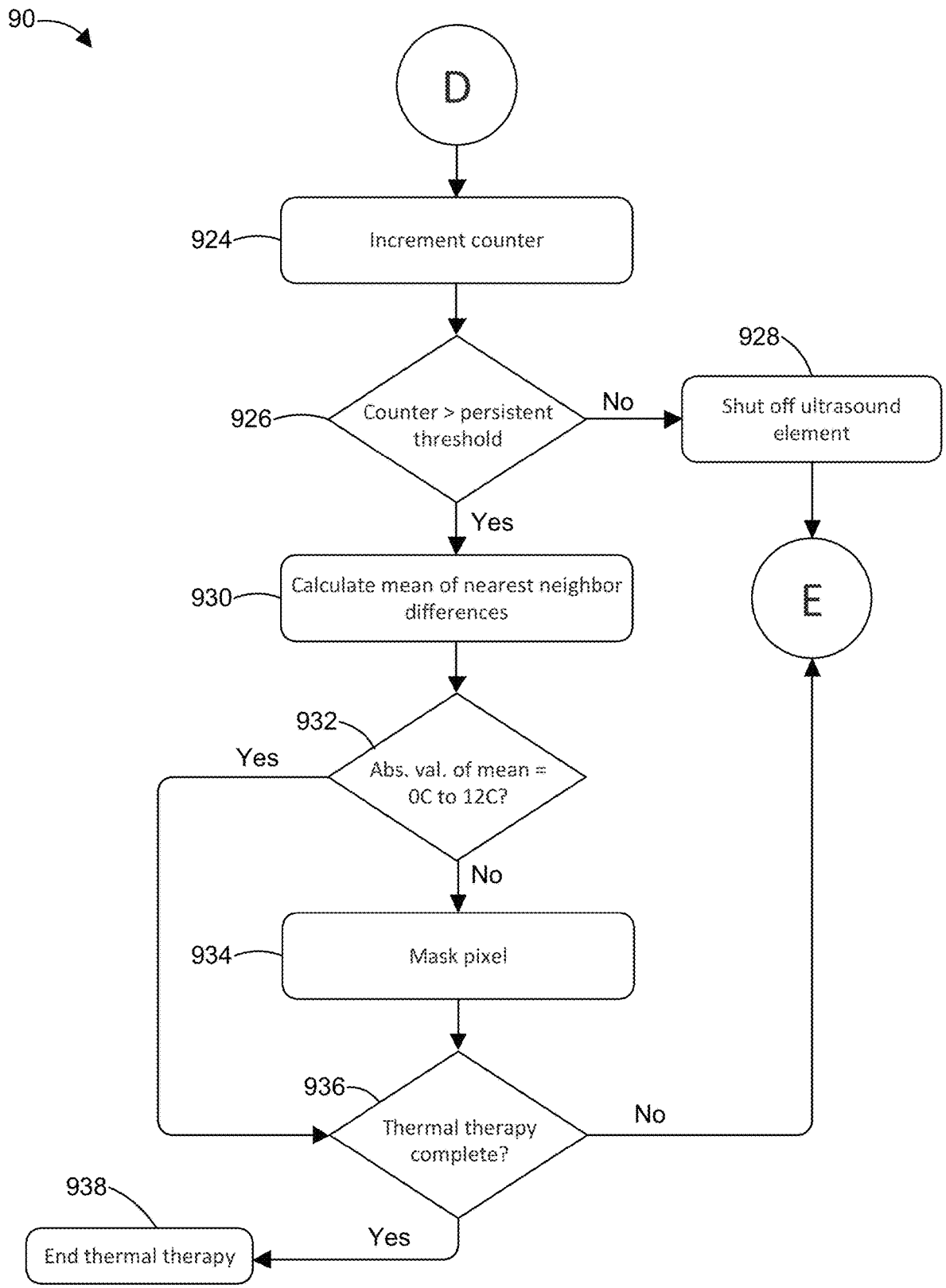

FIGS. 9-11 are a flow chart 90 for applying thermal therapy to a target volume with dynamic pixel masking. In step 900, thermal therapy is delivered from a thermal therapy applicator (e.g., an ultrasound transducer array device in or proximal to the desired target volume), as discussed above. The thermal therapy can be delivered according to a treatment plan, for example as discussed above. In step 902, MRI phase images of a cross-sectional slice of the target volume are collected from an MRI device during a collection period (e.g., a dynamic). The MRI phase images can be received by a computer that is operatively coupled or connected to the MRI device (e.g., over a wired or a wireless connection, such as a network connection, a direct physical connection (e.g., a cable), or other connection). The MRI phase images correspond to MRI temperature data or MRI thermometry data for the slice. In step 904, a temperature map is processed for the slice.

In step 906, the computer evaluates the MRI thermometry data for the slice on a pixel-by-pixel basis. In the first time through flow chart 90, a first pixel is selected in step 906. Another pixel is selected in each subsequent time through flow chart 90 until all pixels have been processed.

In step 908, the computer determines whether the selected pixel is within the temperature control region. As discussed above, the temperature control region (e.g., temperature control region 412) can be defined between the treatment boundary and the central region surrounding the applicator.

If the selected pixel is outside of the temperature control region in step 908, it is ignored in step 910. After step 910, the flow chart 90 returns to step 906 to select another pixel.

If the selected pixel is within the temperature control region in step 908, the flow chart 90 proceeds to step 912 where the computer determines whether any image shift correction is needed as a result of spatial drift with respect to the reference image. The amount of spatial drift can be determined by calculating or otherwise determining a measure of similarity between the current dynamic and the reference image, which may be determined by calculating or otherwise determining a cross-correlation between a Fourier transform of the current dynamic and a Fourier transform of the reference image. In at least some embodiments, the result of the cross-correlation is an image that contains a peak, the location of which is equal to or otherwise defines the amount of spatial shift between the two images. In some embodiments, all slices are processed substantially together or at the same time at the end of a dynamic. In other embodiments, each slice is processed on its own and the slices are thus processed serially. Additional details regarding image shifting are described below with respect to FIG. 12 and in U.S. patent application Ser. No. 15/788,414, titled "Processing System and Dynamic Correction Method for Thermal Therapy," filed on Oct. 19, 2017, which is hereby incorporated by reference.

If image shift correction is needed, the flow chart 90 proceeds to placeholder A. Otherwise, the flow chart 90 proceeds to placeholder B.

From placeholder A, the flow chart 90 proceeds to step 914 (FIG. 10) where the computer determines whether the total or accumulated image shift of the current dynamic with respect to the reference image (e.g., a reference dynamic) is greater than a half pixel. If so, then the locations, in the current dynamic and/or in the current thermometry slice, of the masked pixels (e.g., pixels masked in prior iterations through flow chart 90 or otherwise masked) and the data (e.g., counter) associated with each pixel are image shifted accordingly in step 916. The determination in step 914 and/or the image shifting in step 916 can optionally be stored in the memory so the computer does not need to re-process these steps for each pixel within the same cross-sectional slice and/or within the same dynamic.

Figure 12:
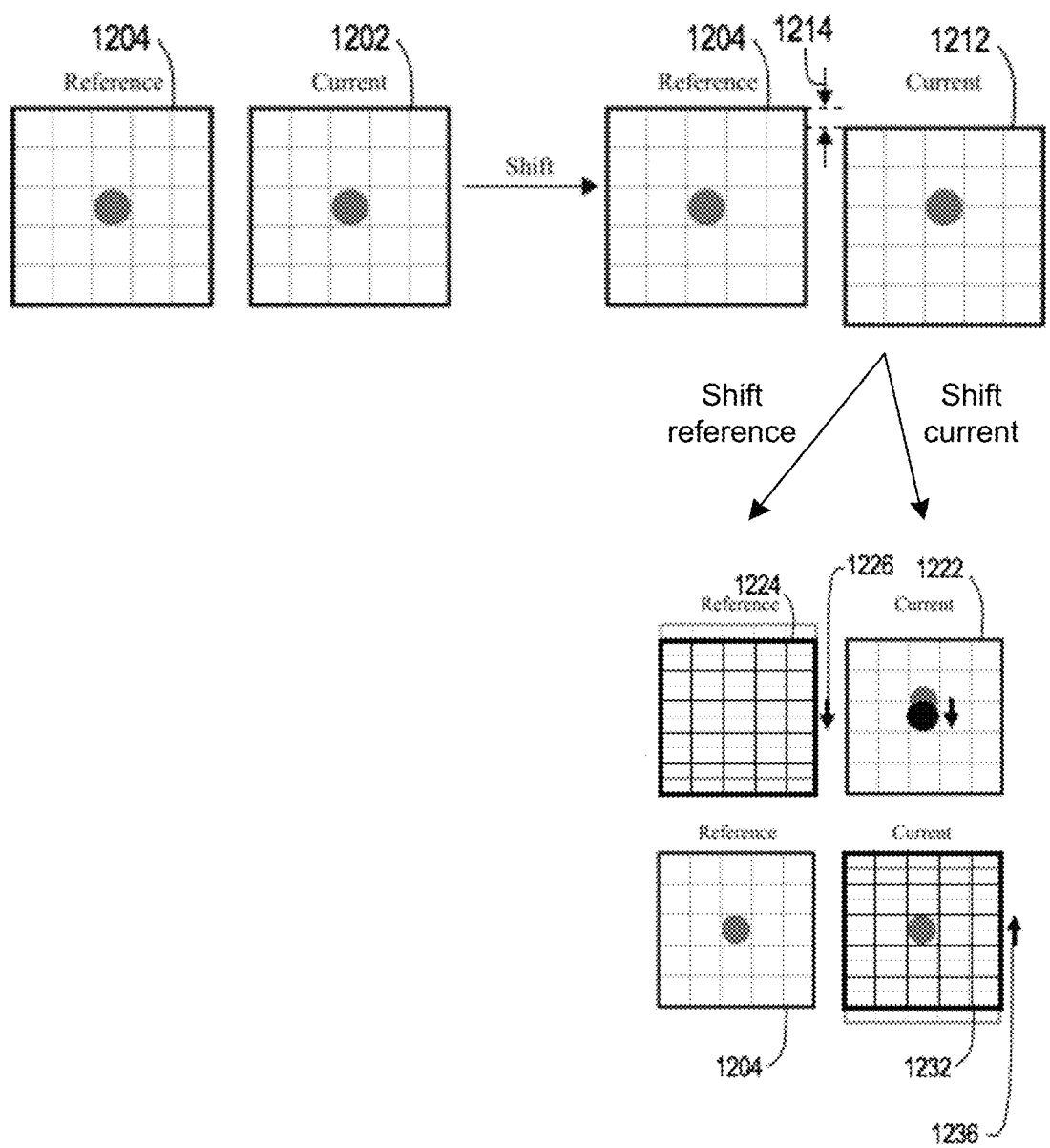
FIG. 12 is a representation showing a current image and a corresponding reference image prior to any spatial drift, and an alternative current image as a result of spatial drift, in accordance with some embodiments.

FIG. 12 is a representation 1200 showing a current image 1202 and a corresponding reference image 1204 prior to any spatial drift, and an alternative current image 1212 as a result of spatial drift 1214, in accordance with some embodiments. In a magnetic resonance imaging (MRI) environment, field drift causes resulting images to be seen to be moving (spatially), which complicates baseline image comparisons.

Therefore, in at least some embodiments, the amount of spatial drift between the current dynamic and the reference image is determined every Y dynamics (or if not periodically, at least from time to time).

The amount of spatial drift may be determined by calculating or otherwise determining a measure of similarity between the current dynamic and the reference image, which may be determined by calculating or otherwise determining a cross-correlation between a Fourier-transform of the current dynamic and a Fourier-transform of the reference image. In at least some embodiments, the result of the cross-correlation is an image that contains a peak, the location of which is equal to or otherwise defines the amount of spatial shift between the two images. If the amount of the spatial shift is greater than 0.5 pixel (or other chosen threshold) (e.g., as determined in step 914), it is necessary (or at least desirable) to spatially register the current dynamic and the reference image.

In accordance with at least some embodiments, two approaches are possible: either align the reference image onto the current image, or align the current image onto the reference image. If the amount of spatial shift is less than 1 pixel, spatially registering the current dynamic and the reference image may employ interpolation such as but not limited to linear interpolation. Other techniques for image shifting include shifting a reference image (instead of an actual acquired image) using interpolation methods as mentioned including without limitation: linear interpolation, cubic splines, or others.

FIG. 12 shows (a) a compensated reference image 1224 after compensation 1226 thereto and a compensated current image 1222 as a result of the compensation to the reference image, corresponding to the first approach, and (b) a compensated current image 1232 as a result of compensation 1236 thereto without any change to the reference image 1204, corresponding to the second approach, in accordance with some embodiments.

Returning to FIG. 10, after step 916 or if step 914=no (i.e., the accumulated image shift of the current dynamic with respect to the reference image is less than or equal to a half pixel in step 914), the flow chart 90 proceeds to step 918 to determine if the pixel is already masked (e.g., if it was masked in a prior dynamic). Step 918 is also reached starting from placeholder B (if no image shift correction is needed). Step 918 can be performed by the computer by querying memory and/or a database that is/are operably coupled to the computer. If the selected pixel is already masked in step 918, the selected pixel is ignored in step 910 (via placeholder C).

In step 920, the computer determines if the selected pixel's temperature (e.g., its corrected temperature) is higher than a maximum temperature limit. The maximum temperature limit can be a predetermined limit that can be related to patient safety, treatment efficiency, and/or treatment efficacy. For example, the maximum temperature limit can be lower the boiling point of tissue and/or liquid in the target volume, which is approximately equal to the boiling point of water (100° C.). In some embodiments, the maximum temperature limit can be from about 80° C. to about 90° C., such as about 82° C., about 84° C., about 86° C., about 88° C., or another temperature between any two of the foregoing temperatures including about 85° C. to about 90° C. In some embodiments, the maximum temperature limit can be set by an operator or other user. In addition, the maximum temperature limit can have a default value (e.g., from about 80° C. to about 90° C.), which can be modified by the operator or other user.

If the selected pixel's temperature (e.g., its corrected temperature) is less than or equal to the maximum temperature limit in step 920, the selected pixel's counter is reset in step 922. The counter represents the number of successive dynamics in which the selected pixel's temperature (e.g., its corrected temperature) is higher than the maximum temperature limit. In step 940, the computer optionally turns back on the ultrasound element that was shut off in step 928 (described below) since the measured temperature of the selected pixel is now at or below the maximum temperature limit. Following step 940, the selected pixel is ignored in step 910 (via placeholder C).

If the selected pixel's temperature (e.g., its corrected temperature) is higher than the maximum temperature limit in step 920, the flow chart 90 proceeds to placeholder D. From placeholder D, the flow chart 90 proceeds to step 924 where the computer increments the selected pixel's counter by 1. For example, if this is the first iteration through flow chart 90 or if the selected pixel's counter was reset in step 922 in the last dynamic, the selected pixel's counter is incremented from 0 to 1.

In step 926, the computer determines whether the selected pixel's counter is higher than a persistent threshold count. The persistent threshold count corresponds to a maximum acceptable number of successive dynamics in which the selected pixel's temperature (e.g., its corrected temperature) is higher than the maximum temperature limit. The persistent threshold count can be from 4 to 8, including 5, 6, or 7. The persistent threshold count can be another number in other embodiments. If the selected pixel's counter is less than or equal to the persistent threshold count, the flow chart 90 proceeds to step 928 where the computer shuts off the ultrasound element that insonifies the treatment volume that includes the selected pixel to allow the treatment volume to cool (e.g., until the measured temperature of the selected pixel is lowered to the maximum temperature limit (or below) as determined in step 920). For example, the computer can generate a control signal or a command that causes the power and/or driving signals to the ultrasound element to be shut off. After the ultrasound element is turned off, the flow chart 90 returns to step 906 (via placeholder E) where the next pixel is selected for processing. If the selected pixel's counter is higher than the persistent threshold count, the flow chart 90 proceeds to step 930.

In step 930, the computer calculates the mean (average) of the temperature differences between the selected pixel and each of its nearest neighbors in the temperature slice. For example, the nearest neighbors can include the pixels above, below, and on either side of the selected pixel in the cross-sectional temperature slice. For example, in the example cross-sectional temperature slice 1300 illustrated in FIG. 13, the selected pixel is located at position C3 (column C, row 3) and its nearest neighbors are located at positions C2, C4, B3, and D3. The average of the temperature differences can be calculated as:

$$\text{Average\_Temp\_Diff} = \frac{(T_{C3} - T_{C2}) + (T_{C3} - T_{C4}) + (T_{C3} - T_{B3}) + (T_{C3} - T_{D3})}{4}$$

where $T_{C2}$, $T_{C4}$, $T_{B3}$, and $T_{D3}$ are the measured temperatures (e.g., the corrected measured temperatures) at pixels C2, C4, B3, and D3, respectively. Using the temperature values in example thermometry slice 1300, the average of the temperature differences is $$\text{Average\_Temp\_Diff} = \frac{(88 - 68) + (88 - 90) + (88 - 64) + (88 - 67)}{4}$$

or 15.75° C.

In some embodiments, the nearest neighbors can include the pixels that are located diagonally from the selected pixel (e.g., pixels B2, D2, B4, and/or D4 in example thermometry slice 1300). In addition, the mean of the temperature differences can be determined over more than one dynamic. For example, the mean of the temperature differences can be based on the temperature differences between the selected pixel and its nearest neighbors in the current dynamic and the temperature differences between the selected pixel (the selected pixel's temperature in the current dynamic or the selected pixel's temperature in a prior dynamic) and its nearest neighbors in one or more prior dynamics (e.g., the last dynamic). In some embodiments, the mean of the temperature differences can also be based on the difference between the selected pixel's temperature in the current dynamic and its temperature in one or more prior dynamics.

In other embodiments, the standard deviation and/or another statistic relating to the temperatures at the selected pixel and its nearest neighbors, which can include one or more dynamics, can be determined in addition to or instead of the mean of the temperature differences between the selected pixel and each of its nearest neighbors in the current dynamic.

It is noted that temperatures are not illustrated in rows 1 and 5 and in column A for clarity purposes only.

In step 932, the computer determines whether the absolute value of the mean of the temperature differences between the selected pixel and each of its nearest neighbors in the current dynamic is within a predetermined temperature range (e.g., between a first predetermined temperature and a second predetermined temperature). For example, the predetermined temperature range can include 0° C. to about 6° C., 0° C. to about 8° C., 0° C. to about 10° C., 0° C. to about 12° C., 0° C. to about 14° C., or another temperature range. In the alternative, the computer can determine whether the absolute value of the temperature differences is greater than a maximum temperature variation, such as about 6° C., about 8° C., about 10° C., about 12° C., about 14° C., or another temperature variation.

In some embodiments, the computer does not need to determine the absolute value of the temperature differences, in which case predetermined temperature range can include about −6° C. to about 6° C., about −8° C. to about 8° C., −10 C to about 10° C., about −12° C. to about 12° C., about −14° C. to about 14° C., or another temperature range.

If the absolute value of the mean of the temperature differences, determined in step 932 (i.e., step 932=no), is outside of the predetermined temperature range, this is an indication that the selected pixel is noisy or inaccurate (e.g., the temperature at the selected pixel is significantly different than the temperatures measured at the neighboring pixels) and the temperature measurement at the selected pixel is unreliable for process control purposes. Accordingly, the selected pixel is "masked" in step 934 and it will be ignored in future dynamics (and future iterations through flow chart 90) until the end of the treatment segment. The treatment segment can comprise a full or a partial treatment whereby a new segment begins with the acquisition of a new reference image.

In some embodiments, when the selected pixel is masked in step 934, the temperature at the selected pixel is replaced with the average temperature of the nearest neighbors. This replacement temperature can be used when the average of the temperature difference between one of the nearest neighbors and its nearest neighbors needs to be calculated. For example, in example thermometry slice 1300, pixel C3 can be replaced with the average temperature of pixels C2, D3, C4, and B3 (i.e., 64° C., 68° C., 67° C., and 90° C., respectively), which is 72.3°. If in a future dynamic the temperature at pixel C2 is above the maximum temperature limit for longer (more counts) than the persistent threshold count, the temperature at pixel C3 can be replaced with the average temperature of the nearest neighbors' pixels. The replacement temperature can be static or constant (e.g., using the average temperature of the nearest neighbors' pixels in the dynamic in which the selected pixel is masked for all future dynamics) or it can be dynamic (e.g., using the average temperature of the nearest neighbors' pixels in the current dynamic (e.g., in the dynamic presently being processed in flow chart 90).

If the absolute value of the mean of the temperature differences, determined in step 932 (i.e., step 932=yes), is within the predetermined temperature range, this is an indication that the selected pixel is not noisy and is accurate (e.g., the temperature at the selected pixel is within an acceptable range of the temperatures measured at the neighboring pixels) and the temperature measurement at the selected pixel is reliable for process control purposes. Accordingly, the flow chart 90 proceeds from step 932 to step 936, to bypass step 934 (i.e., the selected pixel is not masked) so the selected pixel can be considered in future dynamics (and future iterations through flow chart 90). It is noted that since the counter for the selected pixel is not reset, the selected pixel will be reevaluated (e.g., in steps 930 and 932) in the next dynamic if the temperature at the selected pixel remains above the maximum temperature limit (as determined in step 920).

In some embodiments, the computer can evaluate one or more rules over a rolling window of dynamics to determine whether to mask the selected pixel. For example, the computer can determine whether step 932=no (absolute value of the mean of the temperature differences is within the predetermined temperature range) for a threshold number of dynamics over the rolling window of dynamics. In a specific example, the computer can determine whether, for the selected pixel, step 932=no for 8 of the last 10 dynamics or another statistic.

In some embodiments, the computer can track the total number of pixels that are masked and/or the percentage of pixels that are masked and generate an alert if the total number or percentage is greater than a first predetermined threshold value. The total number of pixels and/or the percentage of pixels that are masked can be evaluated for a given slice and/or for the entire dynamic. In some embodiments, the computer can automatically pause thermal therapy treatment if the if the total number or percentage is greater than a second predetermined threshold value, the second predetermined threshold value greater than the first predetermined threshold value.

After the selected pixel is masked in step 934 or following step 932 (if step 932=yes), the computer optionally determines whether the thermal therapy treatment is complete in step 936. The computer can determine whether the thermal therapy is complete based on whether the entire target volume (e.g., each pixel in each cross-sectional slice of the target volume) has received a minimum therapeutic thermal dose and/or whether the entire target volume has reached a minimum therapeutic temperature at some moment during the therapy. The minimum therapeutic temperature can be from about 50° C. to about 70° C. in some embodiments, including about 55° C., about 60° C., about 75° C., and any temperature or temperature range between any two of the foregoing temperatures.

If the thermal therapy treatment is incomplete, the flow chart 90 returns to step 906 (via placeholder E) where the next pixel is selected for processing in step 906 and thermal therapy continues to be delivered to the target volume by the thermal therapy applicator. If the thermal therapy treatment is complete, the thermal therapy treatment is terminated in step 938.

Figure 14:
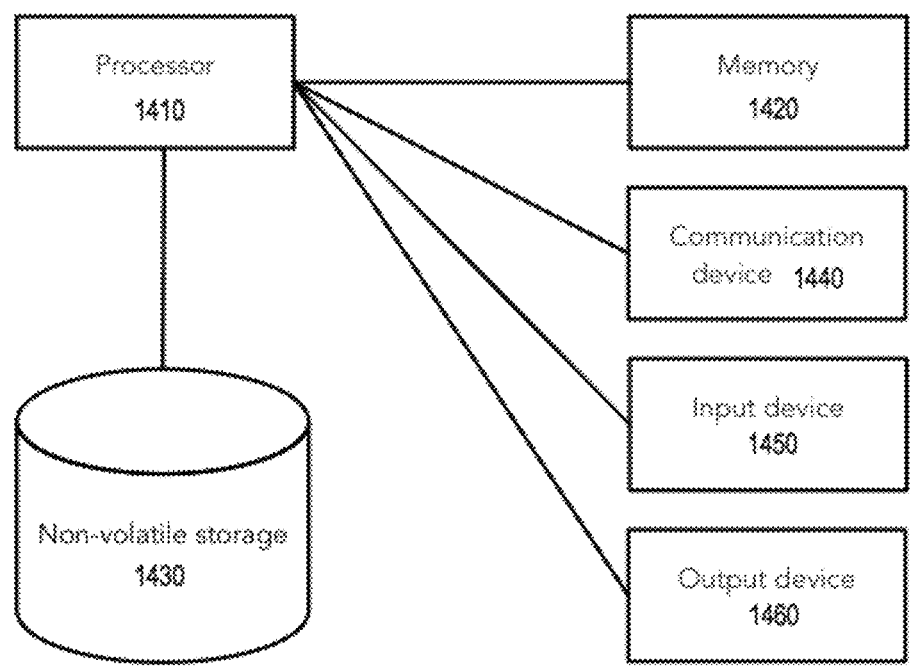
FIG. 14 is a block diagram of a computer architecture according to one or more embodiments.

FIG. 14 is a block diagram of a computer architecture 1400 according to one or more embodiments. In some embodiments, one or more of the systems (or portion(s) thereof), apparatus (or portion(s) thereof) and/or devices (or portion(s) thereof) disclosed herein can have an architecture that is the same as and/or similar to one or more portions of the architecture 1400.

In some embodiments, one or more of the methods (or portion(s) thereof) disclosed herein can be performed by a system, apparatus and/or device having an architecture that is the same as or similar to the architecture 1400 (or portion(s) thereof). The architecture can be implemented as a distributed architecture or a non-distributed architecture.

Referring to FIG. 14, in accordance with at least some embodiments, the architecture 1400 can include one or more processors 1410 and one or more articles of manufacture that comprise non-transitory computer-readable storage media (e.g., memory 1420 and one or more non-volatile storage media 1430). The processor 1410 can control writing data to and reading data from the memory 1420 and the non-volatile storage device 1430 in any suitable manner, as the aspects of the disclosure provided herein are not limited in this respect. The storage media may store one or more programs and/or other information for operation of the architecture 1400. In at least some embodiments, the one or more programs include one or more instructions to be executed by the processor 1410 to provide one or more portions of one or more tasks and/or one or more portions of one or more methods disclosed herein. In some embodiments, other information includes data for one or more portions of one or more tasks and/or one or more portions of one or more methods disclosed herein. To perform any of the functionality described herein, the processor 1410 can execute one or more processor-executable instructions stored in one or more non-transitory computer-readable storage media (e.g., the memory 1420), which may serve as non-transitory computer-readable storage media storing processor-executable instructions for execution by the processor 1410.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices (e.g., communication device 1440), which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices (e.g., input device 1450) and/or one or more output devices (e.g., output device 1460). These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method for controlling thermal therapy, comprising:
using a thermal therapy applicator, delivering a thermal therapy dose to a target volume within a patient's body; and
in a computer:
 (i) receiving, at a first point in time, a first cross-sectional slice of temperature data for pixels corresponding to respective spatial locations in the target volume, wherein at least one pixel in the first cross-sectional slice is unmasked and has a respective measured temperature higher than a maximum temperature limit;
 (ii) determining whether each pixel in the first cross-sectional slice is masked or unmasked;

(iii) determining whether a respective measured temperature of a first unmasked pixel in the first cross-sectional slice is higher than the maximum temperature limit;
(iv) when the respective measured temperature at the first unmasked pixel in the first cross-sectional slice is higher than the maximum temperature limit, increasing a respective pixel counter associated with the first unmasked pixel in the first cross-sectional slice,
(v) when the respective pixel counter associated with the first unmasked pixel is higher than a persistent threshold count, calculating an average temperature difference between a first measured temperature at the first unmasked pixel in the first cross-sectional slice and measured temperatures at neighboring pixels in the first cross-sectional slice;
(vi) applying a mask to the first unmasked pixel when an absolute value of the average temperature difference is greater than a maximum temperature difference;
(vii) repeating steps (iii)-(vi) for each unmasked pixel remaining in the first cross-sectional slice; and
(viii) determining the respective measured temperature at only the unmasked pixels remaining after step (vii); and
stopping the delivery of the thermal therapy to the target volume when the respective measured temperature at each unmasked pixel has reached a minimum therapeutic temperature.

2. The method of claim 1, further comprising:
temporarily shutting off power to an ultrasound element on the thermal therapy applicator when the first measured temperature at the first unmasked pixel in the first cross-sectional slice is greater than the maximum temperature limit, the ultrasound element insonifying a spatial location that corresponds to the first unmasked pixel, whereby the spatial location that corresponds to the first unmasked pixel is cooled.

3. The method of claim 2, further comprising providing power to the ultrasound element when the first measured temperature at the first unmasked pixel is less than or equal to the maximum temperature limit.

4. The method of claim 2, further comprising resetting the first pixel counter when the first measured temperature at the first unmasked pixel is less than or equal to the maximum temperature.

5. The method of claim 1, wherein the maximum temperature limit is within a temperature range of about 80° C. to about 100° C.

6. The method of claim 5, wherein the maximum temperature limit is about 86° C.

7. The method of claim 1, wherein the persistent threshold count is within a range of 4 to 8.

8. The method of claim 7, wherein the persistent threshold count is 6.

9. The method of claim 1, wherein the maximum temperature difference is within a range of 4° C. to about 20° C.

10. The method of claim 9, wherein the maximum temperature difference is about 12° C.

11. The method of claim 1, wherein the minimum therapeutic temperature is within a temperature range of about 50° C. to about 70° C.

12. The method of claim 1, wherein:
the first cross-sectional slice of temperature data comprises an uncorrected temperature at each pixel,
the temperature data comprises magnetic resonance (MR) thermometry data received from an MR imaging (MRI) machine, and
the method further comprises correcting fora drift of a magnetic field of the MRI machine for each uncorrected temperature to determine the respective measured temperature.

13. The method of claim 1, further comprising:
receiving, at a second point in time, a subsequent cross-sectional slice of temperature data for the pixels corresponding to the respective spatial locations in the target volume;
replacing a respective subsequent measured temperature at each masked pixel in the subsequent cross-sectional slice with a respective substitute calculated temperature, each substitute calculated temperature calculated from the respective subsequent measured temperatures at respective neighboring pixels, in the corresponding subsequent cross-sectional slice, to each masked pixel.

14. The method of claim 13, wherein:
the average temperature difference is a first average temperature difference;
the neighboring pixels are first neighboring pixels; and
the method further comprises:
  (i) determining whether each pixel in the subsequent cross-sectional slice is masked or unmasked;
  (ii) determining whether a respective subsequent measured temperature of a first unmasked pixel in the subsequent cross-sectional slice is higher than the maximum temperature limit;
  (iii) when the respective subsequent measured temperature at the first unmasked pixel in the subsequent cross-sectional slice is higher than the maximum temperature limit, increasing a respective pixel counter associated with the first unmasked pixel in the subsequent cross-sectional slice;
  (iv) when the respective pixel counter associated with the first unmasked pixel in the subsequent cross-sectional slice is higher than the persistent threshold count, calculating a second average temperature difference between the subsequent measured temperature at the first unmasked pixel in the subsequent cross-sectional slice, and the measured temperatures at second neighboring pixels in the subsequent cross-sectional slice, wherein the second neighboring pixels comprise a first masked pixel and the measured temperature at the first masked pixel is a first substitute calculated temperature;
  (v) applying a mask to the first unmasked pixel in the subsequent cross-sectional slice when an absolute value of the second average temperature difference is greater than the maximum temperature variation; and
  (vi) repeating steps (ii)-(v) for each unmasked pixel remaining in the subsequent cross-sectional slice.

15. The method of claim 1, further comprising defining at least one reference image and at least one current image, and spatially shifting said reference image relative to said current image so as to correct for a drift with respect to the spatial locations in the target volume.

16. The method of claim 1, further comprising image-shifting each pixel in the first cross-sectional slice when an accumulated image shift of a first dynamic, with respect to a reference dynamic, is greater than a threshold value, the first dynamic comprising the first cross-sectional slice.

17. A system for thermal therapy, comprising:
a thermal therapy applicator, configured to deliver a thermal therapy dose to a target volume within a patient's body; and
a computer having at least a processor, a data store and a data communication interface;
the computer configured and arranged to execute in said processor, machine-readable instructions, and to operate on data obtained over said data communication interface and stored in said data store;
the computer further configured and arranged as above to:
(i) receive, at a first point in time, a first cross-sectional slice of temperature data for pixels corresponding to respective spatial locations in the target volume;
(ii) determine whether each pixel in the first cross-sectional slice is masked or unmasked;
(iii) determine whether a respective measured temperature of a first unmasked pixel in the first cross-sectional slice is higher than a maximum temperature limit;
(iv) when the respective measured temperature at the first unmasked pixel in the first cross-sectional slice is higher than the maximum temperature limit, increasing a respective pixel counter associated with the first unmasked pixel in the first cross-sectional slice,
(v) when the respective pixel counter associated with the first unmasked pixel is higher than a persistent threshold count, calculate an average temperature difference between a first measured temperature at the first unmasked pixel in the first cross-sectional slice and measured temperatures at neighboring pixels in the first cross-sectional slice;
(vi) apply a mask to the first unmasked pixel when an absolute value of the average temperature difference is greater than a maximum temperature difference;
(vii) repeat steps (iii)-(vi) for each unmasked pixel remaining in the first cross-sectional slice; and
(viii) determine the respective measured temperature at only the unmasked pixels remaining after step (vii); and
the computer further configured to stop the delivery of the thermal therapy to the target volume when the respective measured temperature at each unmasked pixel has reached a minimum therapeutic temperature.

18. The system of claim 17, wherein the thermal therapy applicator comprises an ultrasound thermal therapy apparatus that delivers ultrasonic energy to the target volume and the ultrasound therapy apparatus is controlled by the computer according to said claim 17.

* * * * *